United States Patent [19]

Fischer et al.

[11] 4,302,480
[45] * Nov. 24, 1981

[54] THIN COVER SHEET FOR USE IN MICROSCOPIC STAINING AND A PROCESS FOR ITS PRODUCTION

[75] Inventors: Wolfgang Fischer, Darmstadt; Brigitte Wissel, Darmstadt-Eberstadt, both of Fed. Rep. of Germany

[73] Assignee: Merck Patent Gesellschaft mit Beschrankter Haftung, Darmstadt, Fed. Rep. of Germany

[*] Notice: The portion of the term of this patent subsequent to Jun. 23, 1998, has been disclaimed.

[21] Appl. No.: 49,010

[22] Filed: Jun. 15, 1979

[30] Foreign Application Priority Data

Jun. 16, 1978 [DE] Fed. Rep. of Germany ....... 2826363

[51] Int. Cl.$^3$ .................... G01N 1/00; G01N 1/30
[52] U.S. Cl. .................... 427/2; 424/2; 424/3; 424/7; 424/78; 424/80; 427/4; 156/57
[58] Field of Search ............ 424/2, 3, 7, 78, 80-83; 427/4; 156/57

[56] References Cited

U.S. PATENT DOCUMENTS

| | | | |
|---|---|---|---|
| 2,155,658 | 4/1939 | Herrman | 424/78 |
| 2,992,971 | 7/1961 | Millman | 424/3 |
| 3,495,926 | 2/1970 | Naz | 424/3 |
| 3,498,860 | 3/1970 | Pickett | 424/3 |
| 3,678,151 | 7/1972 | Horonick | 424/3 |
| 3,701,633 | 10/1972 | Davis | 23/253 TP |
| 3,737,335 | 6/1973 | Feinberg | 424/3 |
| 3,768,978 | 10/1973 | Grubb | 23/259 |
| 3,796,594 | 2/1974 | Thomae | 424/3 |
| 3,937,613 | 2/1976 | Rosicky | 23/253 TP |
| 3,980,436 | 9/1976 | Greenfield | 23/253 R |
| 4,103,041 | 7/1978 | Macho | 424/3 |

FOREIGN PATENT DOCUMENTS

| | | | |
|---|---|---|---|
| 1037725 | 8/1958 | Fed. Rep. of Germany . | |
| 2737845 | 3/1978 | Fed. Rep. of Germany | 424/3 |
| 2818826 | 11/1978 | Fed. Rep. of Germany . | |

OTHER PUBLICATIONS

Schmidt–Brucken, Chem. Zeit., vol. 97, 1973, pp. 200-205.
Emmel & Cowdry, Lab. Tech. in Biol. & Med., Krieger Pub. Co., Huntington, N.Y., 1970, (fas pp. 359,360).
Zirkle, Stain Tech., vol. 15, 1940, pp. 139-153.
Huber, Arch. Derm. & Syph., vol. 56, 1947, pp. 763-765.
Traub, Plant Life, vol. 7, 1951, pp. 155-157.
Isaac, Stain Tech., vol. 33, 1958, pp. 261-264.

*Primary Examiner*—Anna P. Fagelson
*Attorney, Agent, or Firm*—Millen & White

[57] ABSTRACT

A thin cover sheet for use in microscopic staining consists essentially of a transparent, water-insoluble plastic carrier and a coating thereon comprising a colorant, and at least one polymer which is soluble both in water and in lower aliphatic alcohols. A method of microscopic staining comprises applying an aqueous solution or a lower aliphatic alcohol solution onto the side of a microscopic plate containing a test sample to be stained or onto the coating of such a thin cover sheet for use in the microscopic staining and contacting the test sample side of the microscopic plate and the coating side of the thin cover sheet.

6 Claims, No Drawings

THIN COVER SHEET FOR USE IN MICROSCOPIC STAINING AND A PROCESS FOR ITS PRODUCTION

BACKGROUND OF THE INVENTION

The present invention relates to a new thin cover sheet for use in microscopic staining methods and to a new process for its production.

Glass microscope slides coated with dyestuff for staining biological samples which are to be identified and evaluated under a microscope have been described for a long time. However, the production of correspondingly coated thin cover sheets made of organic material has proved to be difficult. Yet, such sheets are attractive for various reasons; for example from price considerations (less expensive raw materials and possibilities for simpler and continuous production).

Several problems were encountered. The viscosity of the solutions, in water or organic solvents, of the dyestuffs to be applied were frequently too low; therefore, in order to obtain usable stainings, the application of the solution had to be repeated so often that the original price advantages were virtually eliminated. Frequently, poor or incomplete wetting of the thin sheet occurred and resulted in a non-uniform coating of the thin sheet and thus in unusable stainings. The addition of emulsifiers also did not always result in success. Readily soluble dyestuffs were flushed to the edges when the thin film was placed on the moistened microscope slide and were then deficient in the middle when staining was carried out.

SUMMARY OF THE INVENTION

Accordingly, it is an object of the present invention to develop thin cover sheets for use in microscopic staining methods, which do not have the above-mentioned disadvantages and which, in particular, are uniformly coated.

Upon further study of the specification and appended claims, further objects and advantages of this invention will become apparent to those skilled in the art.

These objects have been attained by providing a thin cover sheet for use in microscopic staining consisting essentially of a transparent, water-insoluble plastic carrier and a coating thereon comprising a colorant, and at least one polymer which is soluble both in water and in lower aliphatic alcohols.

In a method aspect, these objects have been attained by providing a process for producing the above thin cover sheet comprising applying at least one layer of an aqueous-alcoholic solution of the colorant and of the polymer to the plastic carrier, and drying the resulting coating.

The present invention also relates to the use of the thin cover sheet for staining when carrying out microscopic investigations.

DETAILED DISCUSSION

It has been found that the incorporation of specific organic polymers improves the quality of the dye solutions and dye coatings to such an extent that the difficulties mentioned can be regarded as having been overcome. In particular, the dye solutions of this invention are also suitable for application by printing techniques.

Stainings which have been carried out using the thin cover sheets according to this invention offer the same differentiation possibilities as the standard methods conventional hitherto, which were carried out using dyestuff solutions, and are virtually indistinguishable from these. For the practical worker, the advantages of the new stainings, inter alia, include the fact that no separate equipment, for example a staining stage or automatic staining device is required for staining. Further, the irksome handling of dye solutions is dispensed with and staining can always be carried out with the same dyestuff composition. Only per this invention, however, can the standardization desirable in a practical laboratory be achieved.

The process according to this invention is carried out by adding a suitable solvent (for example water or a lower alcohol) to the desired dyestuffs; adding buffer substances or tensides if desired; adding a specific amount of an organic polymer; and dissolving all the constituents of the mixture with stirring. The resulting solution is applied to the thin sheet and dried, for example by air and/or by supplying heat, to give a thin film on the thin sheet.

Other sheet-like compositions have been known; however, all are very different from the subject matter of this invention.

The use of a cover slip which is coated with an adhesive is known from U.S. Pat. No. 3,498,860. When this slip is applied to a microscope slide which has been provided with a stained sample and previously moistened with a tissue-cleansing liquid, the cover slip adheres firmly to the microscope slide. In contrast, the carrier of the thin cover film according to this invention consists of plastic, and the polymer with which this plastic is coated is not an adhesive. Thus, the principle is different.

Furthermore, a sheet-like carrier made of fibrous material, which contains the color reagent in a state of fine division, is described in U.S. Pat. Spec. No. 3,678,151. In use, the carrier is dipped into a solution and placed on the microscope slide, to which the sample has been applied. After staining, the carrier is removed and the sample is examined under the microscope. In contrast to the carrier of this U.S. patent specification which is also available commercially, the thin cover sheet according to this invention does not consist of fibrous material; also, it contains the colorant only in the layer applied to the surface and is therefore of a different composition.

Furthermore, rigid thin transfer sheets for chemical analysis on a microscopically small scale are described in Chemiker-Zeitung 97, 200 to 205 (1973). These thin sheets consist of gelatine or polyvinyl alcohol and contain the detection reagent incorporated therein. In a particular embodiment, these thin sheets are applied to a rigid carrier, for example a carrier made of polyester, and form a thin laminate together with this carrier. In contrast to this, the coating of the thin cover sheet according to this invention contains a polymer which is soluble both in water and in lower aliphatic alcohols. This does not form a thin sheet and is not suitable for reproduction analysis.

Finally, in German Offenlegungsschrift No. 2,515,966 a cover slip made of glass or plastic is described onto which dyestuffs can be sprayed. Application of the dyestuffs by printing techniques, as is possible according to this invention, fails in this case, however, because the viscosity of the dye solution is too low.

Herein, the term "transparent" signifies that, in the measurement range, the particular medium has no adverse influence on the optical characteristics of the substrate to be measured, for example has no characteristic absorption. In addition, a thin cover sheet is understood to mean a thin sheet which is made of a plastic which is more or less elastic and which can be placed on a microscope slide. The colorant coating of the thin cover sheet according to this invention is so arranged that it comes into contact with the biological sample to be stained, on the microscope slide.

The shape of the thin cover sheet is capable of further variation and can be, for example, round or polygonal. Usually, the shape corresponds approximately to that of the microscope slide customarily used, but it can also be smaller. The thickness of the thin cover sheet can be 0.01 to 0.5 mm but is preferably about 0.05 to 0.2 mm.

The material from which the thin cover sheet is made is an appropriately transparent, water-insoluble plastic. It must be of a nature such that as far as possible no reagents are absorbed therein or held fast thereto. Therefore, for example, absorbent carriers, such as are used for reagent papers, cannot be used. In other respects, however, the choice of the material for the thin sheet is not critical. For example, suitable transparent, water-insoluble plastics are polymers and polycondensation products, such as polyvinyl chloride (PVC), polyesters, polyamides, polycarbonates, polystyrene, polyurethanes, polyalkenes, such as polyethylene or polypropylene, polyethylene terephthalate or other high molecular weight organic substances, such as cellulose acetate.

The coating on the thin cover sheet according to the invention has the thinness of a film and can partially or—preferably—entirely cover the side of the thin cover sheet which faces towards the microscope slide. The thickness of the coating can be 0.01 to 0.02 mm and is preferably 0.05–0.15 mm.

Polymers suitable for the coating include all polymers and copolymers of various degrees of polymerization which appear transparent on moistening and are soluble both in water and in lower aliphatic alcohols; for example preferably solid and semi-solid homopolymers of vinylpyrrolidone and vinyl alcohol units; and also polyglycols of units of, for example, ethylene glycol or corresponding copolymers of these and other monomers in various molar ratios, for example copolymers of vinylpyrrolidone and vinyl acetate. Polylactides and corresponding copolymers with the said monomers are also suitable, for example copolymers of lactide and glycolide in various molar ratios. In this context, lower aliphatic alcohols include, preferably, aliphatic alcohols with up to 6 C atoms, for example methanol, ethanol, propanol, isopropanol, butanol, isobutanol, sec-butanol, tert-butanol, pentanol, hexanol or isohexanol.

The solution of the colorant, with the aid of which the coating is produced, and the coating itself can also contain further additives, for example emulsifiers. Suitable additives are, in particular, ionic or especially non-ionic tensides. These substances, some of which are available commercially, can consist, for example, of oxalkylated higher fatty alcohols, for example oxethylated or oxpropylated fatty alcohols with a chain length of 10–20 C atoms; alcohols of this type which can be used are preferably the natural or synthetically accessible, saturated or unsaturated straight-chain alcohols, for example various fractions of coconut fatty alcohol or the fatty alcohols accessible by special hydrogenation of unsaturated fatty acids. Tensides which can be used are appropriately also oxalkylated higher alkylphenols, for example oxethylated octyl-, nonyl- or decyl- phenols, and the oxethylated nonylphenols which are available commercially are preferred.

Colorants which can be employed are, in principle, all dyestuffs and all reagents which give a characteristic coloration with the samples to be detected. In particular, suitable colorants are those substances which with specific biological samples, such as, for example, constituents of the blood, of the tissue, of the connective tissue, various glands and organs, the bone marrow, the bone, the body fat, glycogen and collagen, antibodies, mucuses (for example mucuses of the uterus or of the vagina) or sugars or constituents of plants, micro-organisms (for example bacteria) or protozoa give one of the color-forming agents known from the literature, such as are described in detail, for example, in "Staining Procedures", 3rd edition, edited by George Clark, The Williams & Wilkens Company, Baltimore/U.S.A. 1973 whose disclosure is incorporated by reference herein. The thin cover sheets of this invention are especially suitable for blood staining according to Giemsa, May-Grünwald or Wright, for supravital staining, for bacteria staining according to Gram, for the Ziehl-Neelsen stain for staining acid-resistant bacteria or for the Papanicolaou stain for the examination of specific mucuses (for example vaginal mucus).

The ratio of the amounts of colorant and polymer in the dye solution and—derivable therefrom—in the coating on the thin sheet can vary within wide limits and is in particular dependent on the viscosity of the solution of the colorant and of the polymer to be employed. The lower the viscosity of the dye solution, the more polymer is necessary. Conversely: the more viscous the solution of the polymer, the smaller is the amount of this solution which needs to be added to increase the viscosity of the dyestuff solution. On changing from one polymer to another, more polymer substance is always necessary if the viscosity of the solution of the second polymer at the same concentration is lower than that of the solution of the first polymer.

In general, the amount of organic polymer in the coating of the thin sheet is 0.05–5 g/m$^2$ of the sheet. In the solution of the colorant, the concentration of the organic polymer is preferably about 0.1–10%; however, these values can vary greatly, depending on the colorant used. The coating preferably contains about 1–30% by weight of colorant and especially about 10–20% by weight; however, variations outside these values are again possible, depending on the colorant used.

The solutions of the colorant can be applied to the thin sheet by various methods. Thus, it is possible uniformly to distribute the solution manually, for example using a sponge, on the thin sheet. In place of a sponge, an artist's brush, a cloth or a soft flat brush are also advantageous. Application of the colorant by spraying is also possible. In practice, however, application of the colorant by processes used in printing technology is particularly preferred, for example by the processes, which are in themselves known, of photogravure printing, screen printing or application with rollers. In the case of printing processes with rollers, the dye solution is in the holes of a printing roller which, as a result of suitable measures (wiping off), is otherwise free from dyestuff, and can be transferred to the material of the thin sheet by rotating the roller.

At least one application of the dye solution is made to the thin cover sheet; 5 applications are, for example, certainly possible. However, 3 applications are the rule and are usually adequate for the intended purposes. The viscosity of the final dye solution is about 1–1,000 and preferably 25–500 centipoise. The solution of the dye without the polymer is thickened to such an extent by the addition of the polymer that even solutions in which the colorant is in low concentration can be applied as a uniform coating to the thin sheets.

After applying the colorant to the thin cover sheet, the coating is dried in a conventional manner, for example, in a stream of air and/or by the action of heat or infrared light. Appropriately, drying is carried out in a stream of air at 50°–60° C.

When a stain produced using the thin cover sheet of this invention is evaluated under a microscope, the thin cover sheet can be present or absent, as desired. If staining merely for general information purposes or staining for routine purposes is desired, the thin sheet can be left on the microscope slide when evaluating, for the sake of simplicity. If, on the other hand, it is desired to store the stain, for example for documentation purposes, then, for example, the thin sheet can be removed before evaluating and the stained sample will be washed and then dried.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Thin cover sheet for blood staining according to Giemsa (a) 0.11 kg of Giemsa's azure-eosin-methylene blue and 1.25 kg of a vinylpyrrolidone/vinylacetate copolymer (Luviskol ® K 90) are dissolved at room temperature in a mixture of 50 liters of ethanol and 0.32 liter of a 1% aqueous solution of a fatty alcohol polyglycol ether (Marlipal ®). The dye solution is uniformly distributed on a thin sheet of polyvinyl chloride (thickness 0.1 mm) using a sponge and the coating of dye is dried at 50° C. The application of the dye and drying are repeated once or twice and the thin sheet is cut into pieces 55 mm long and 24 mm wide.

(b) Dye solution is transferred to a thin sheet of polycarbonate from a rotating roller which is continuously dipped into an ethanolic dyestuff solution of Giemsa's azure-eosin-methylene blue prepared analogously to Example 1(a) and any excess of dye solution which may arise is removed using a doctor blade. The thin sheet is then dried and cut into suitable pieces.

The thin sheet can also be coated by printing techniques, for example by screen printing in the conventional manner.

(c) An ethanolic dyestuff solution of Giemsa's azure-eosin-methylene blue prepared analogously to Example 1(a) is sprayed from a nozzle onto a 0.1 mm thick sheet of polyamide which is drawn from a roll past the nozzle. Analogously to Example 1(a), drying is carried out at 50° C. and the thin sheet is cut into pieces (60×20 mm).

EXAMPLE 2

Procedure for using a thin cover sheet for blood staining according to Giemsa

A drop of blood flowing from the ear lobe or finger tip is applied to a cleaned microscope slide and dispersed in the customary manner using a cover slip held at an angle, by drawing the drop of blood along with the cover slip. The blood smear is dried in air and fixed by dipping in methanol or ethanol of 10 seconds. It is then dried. One drop of a buffer solution of pH 6 is now applied to the center of the blood smear and the thin cover sheet according to Example 1(a), (b) or (c) is placed with its dye coating on the blood smear for 10 minutes at room temperature. During this time the buffer solution spreads uniformly in a thin layer between the thin sheet and the smear. The thin dye sheet is then removed and the microscope slide is rinsed with distilled water at pH 7.2 (or with a Weise buffer solution) and dried in air. The blood picture is evaluated under a microscope. The stained blood smear produced in this way can be stored for a relatively long time.

If storing is not desired, it is also possible to evaluate the microscope slide covered with the thin dye sheet directly under the microscope.

EXAMPLE 3

Thin cover sheet for blood staining according to May-Grünwald

Analogously to Examples 1(a), (b) or (c), a thin sheet of polyvinyl chloride is coated with a dyestuff solution which has the following composition: 0.14 kg of May-Grünwald's eosin-methylene-blue, 1.25 kg of vinylpyrrolidone/vinyl acetate copolymer (Luviskol ® K 90), 0.30 liter of a 1% aqueous solution of a nonylphenol polyglycol ether (Marlophen ®) and 50 liters of ethanol.

EXAMPLE 4

Thin cover sheet for blood staining according to Wright

Analogously to Examples 1(a), (b) or (c), a thin sheet of polyvinyl chloride is coated with a dyestuff solution which has the following composition: 0.12 kg of Wright's eosin-methylene-blue, 1.25 kg of a vinylpyrrolidone/vinyl acetate copolymer (Luviskol ® K 90), 0.32 liter of a 1% aqueous solution of a fatty alcohol polyglycol ether (Marlipal ®) and 50 liters of ethanol.

EXAMPLE 5

Thin cover sheets for bacteria staining according to Gram

Analogously to Examples 1(a), (b) or (c), three thin sheets of polyvinyl chloride are coated with dyestuff solutions which have the following compositions:

Colorant solution 1

0.1 kg of crystal violet and 10 liters of ethanol.

Colorant solution 2

0.1 kg of iodine, 0.2 kg of polyglycol (average molecular weight about 4,000), 0.3 kg of a vinylpyrrolidone/vinyl acetate copolymer (Luviskol ® K 90) and 10 liters of ethanol.

Colorant solution 3

0.1 kg of Safranin, 1.2 kg. of a vinylpyrrolidone/vinyl acetate copolymer (Luviskol ® K 90) and 40 liters of ethanol.

EXAMPLE 6

Thin cover sheets for Ziehl-Neelsen staining, for staining acid-resistant bacteria Analogously to Examples 1(a), (b) or (c), two thin sheets of polycarbonate are coated with dyestuff solutions which are prepared as follows:

(a) Fuchsine solution

Successively, 400 g of fuchsine, 300 g of phenol and 200 g of a vinylpyrrolidone/vinyl acetate copolymer (known by the tradename Luviskol ® K 90) are dissolved in 10 liters of ethanol.

(b) Methylene blue solution 30 g of methylene blue are dissolved in 1 liter of water. This solution is then mixed well with a solution of 300 g of a vinylpyrrolidone/vinyl acetate copolymer (Luviskol ® K 90) in 9 liters of ethanol.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A thin cover sheet for use in microscopic staining consisting essentially of a transparent, water insoluble plastic carrier and a dried coating thereon comprising a colorant for microscopic staining, uniformly dispersed within at least one polymer which is soluble both in water and in lower aliphatic alcohols, said colorant and polymer together comprising a mixture whereby, when said cover sheet is placed on a slide supporting a sample with said mixture contacting the sample, said polymer dissolves allowing uniform passage of said colorant to said sample thereby achieving uniform staining of the sample.

2. The thin cover sheet of claim 1, wherein the amount of polymer on the thin sheet is 0.05 to 5 g/m$^2$ of the sheet.

3. The thin cover sheet of claim 1, wherein the polymer consists essentially of homo- or copolymers of vinylpyrrolidone, vinyl alcohol or ethylene glycol or of copolymers of vinylpyrrolidone and vinyl acetate.

4. The thin cover sheet of claim 2 wherein the coating contains 1–30% of colorant.

5. A process for producing the thin cover sheet of claim 1 comprising applying at least one layer of an aqueous-alcoholic solution of the colorant and of the polymer to the plastic carrier, and drying the resulting coating.

6. A method of microscopic staining which comprises applying an aqueous solution or a lower aliphatic alcohol solution onto the side of a microscopic plate containing a test sample to be stained or onto the coating of a thin cover sheet for use in the microscopic staining, said cover sheet having a dried coating thereon comprising a colorant uniformly dispersed within at least one polymer which is soluble both in water and in lower aliphatic alcohols and said colorant and polymer together comprising a mixture, and contacting the test sample side of the microscopic plate and the coating side of the thin cover sheet thereby causing dissolution of the polymer on the thin cover sheet for allowing uniform passage of the colorant to the sample to achieve uniform staining of the sample.

* * * * *